(12) United States Patent
Norton

(10) Patent No.: US 8,429,864 B2
(45) Date of Patent: Apr. 30, 2013

(54) DRYWALL CORNER OR A TRANSITION CORNER

(76) Inventor: Jody Norton, Milton-Freewater, OR (US)

(*) Notice: Subject to any disclaimer, the term of this patent is extended or adjusted under 35 U.S.C. 154(b) by 610 days.

(21) Appl. No.: 10/940,219

(22) Filed: Sep. 13, 2004

(65) Prior Publication Data
US 2006/0053712 A1   Mar. 16, 2006

(51) Int. Cl.
 E04B 1/00 (2006.01)
 E04B 2/00 (2006.01)
 E04C 2/30 (2006.01)

(52) U.S. Cl.
 USPC ............ 52/287.1; 52/254; 52/272; 52/717.05

(58) Field of Classification Search .............. 52/287.1, 52/288.1, 364, 366, 367, 254, 255, 256, 257, 52/272, 717.05, 716.01
See application file for complete search history.

(56) References Cited

U.S. PATENT DOCUMENTS

| | | | |
|---|---|---|---|
| 2,851,741 A * | 9/1958 | Stemples | 52/255 |
| 3,922,408 A * | 11/1975 | Smith | 428/40.1 |
| 4,012,878 A * | 3/1977 | Ellingson | 52/288.1 |
| 4,313,991 A | 2/1982 | Lamb | 428/131 |
| 4,719,732 A | 1/1988 | Bernard | 52/287 |
| 4,977,718 A * | 12/1990 | Hoffman, Sr. | 52/287.1 |
| 5,045,374 A * | 9/1991 | Tucker | 428/83 |
| 5,138,810 A | 8/1992 | Kartler | 52/254 |
| D351,988 S * | 11/1994 | Gotcher | D8/403 |
| 5,904,016 A * | 5/1999 | Koenig et al. | 52/255 |
| 5,916,101 A * | 6/1999 | Stibolt | 52/254 |
| 6,295,776 B1 | 10/2001 | Kunz | 52/255 |
| 6,360,503 B1 * | 3/2002 | Koenig, Jr. | 52/287.1 |
| 6,363,673 B1 * | 4/2002 | Robertson | 52/255 |
| 6,438,914 B1 * | 8/2002 | Robertson | 52/255 |
| 6,539,680 B2 | 4/2003 | Kunz et al. | 52/256 |
| 6,631,597 B1 * | 10/2003 | Rutherford | 52/287.1 |
| 6,684,586 B1 * | 2/2004 | Hoffmann, Sr. | 52/255 |
| 6,691,476 B1 * | 2/2004 | Kunz | 52/287.1 |
| 7,836,644 B2 * | 11/2010 | Cooper | 52/211 |
| D652,955 S | 1/2012 | Budzik | |
| 2002/0035809 A1 * | 3/2002 | Smythe, Jr. | 52/255 |
| 2003/0056455 A1 * | 3/2003 | Harel | 52/287.1 |
| 2005/0081476 A1 | 4/2005 | Budzik | |

OTHER PUBLICATIONS

Trim-Tex Product Catalog, "350, ¾ & 1 ½" Step Adapter (Wood)", http://liveweb.archive.org/http://www.trim-tex.com/product_catalog.php?cat_display=viewcategory&catid=19, at least as early as Jul. 16, 2011.

* cited by examiner

Primary Examiner — Joshua J Michener
Assistant Examiner — Elizabeth A Plummer
(74) Attorney, Agent, or Firm — Law Office of Karen Dana Oste, LLC

(57) ABSTRACT

A transition corner or drywall corner which transitions from a rounded exterior corner to a right angle corner at the trim. The transition corner has an exterior side with depressions which receive mud, an elevated longitudinal bead along an apex of an acute angle of the exterior side which facilitates the receipt of mud. The interior side is shaped to be received by the shape of an exterior corner, which is generally rounded, and is coated with an adhesive means to allow fixing and adjustment of the transition corner at the trim to be in vertical alignment with the exterior corner.

13 Claims, 5 Drawing Sheets

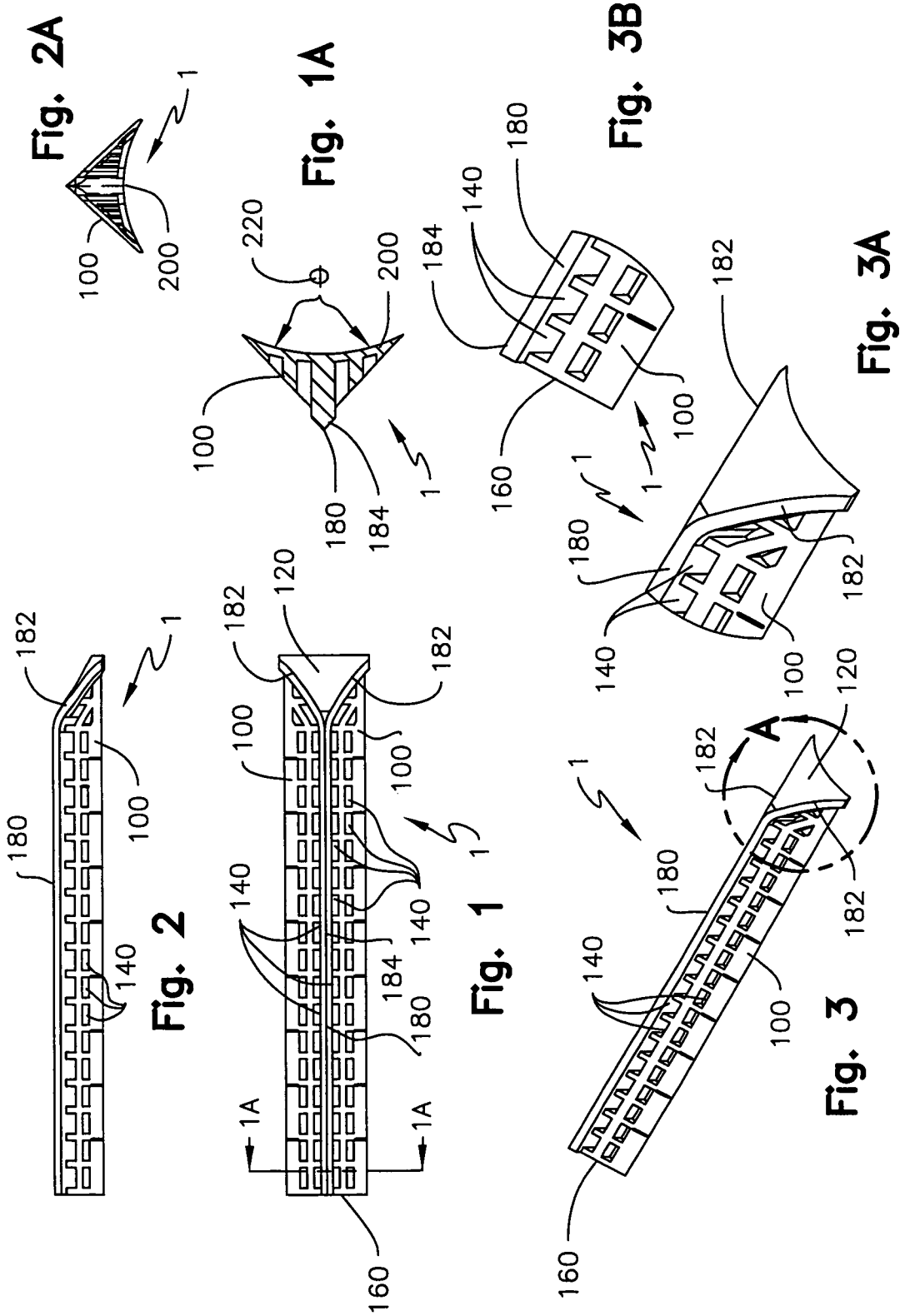

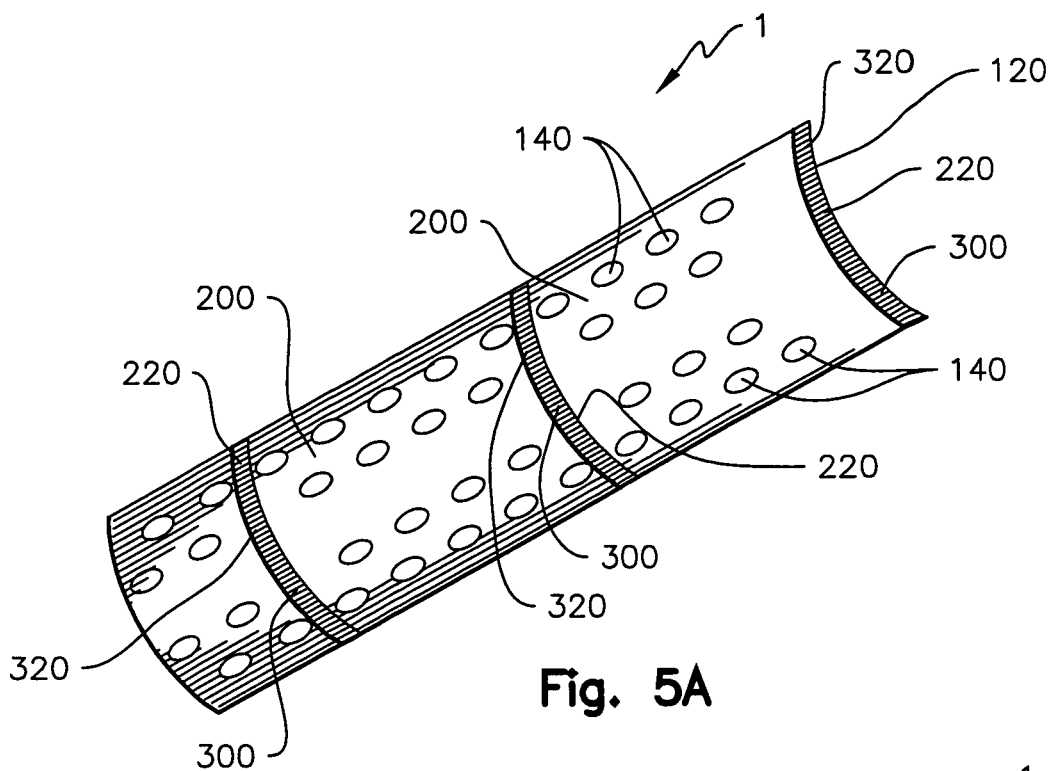
Fig. 5A
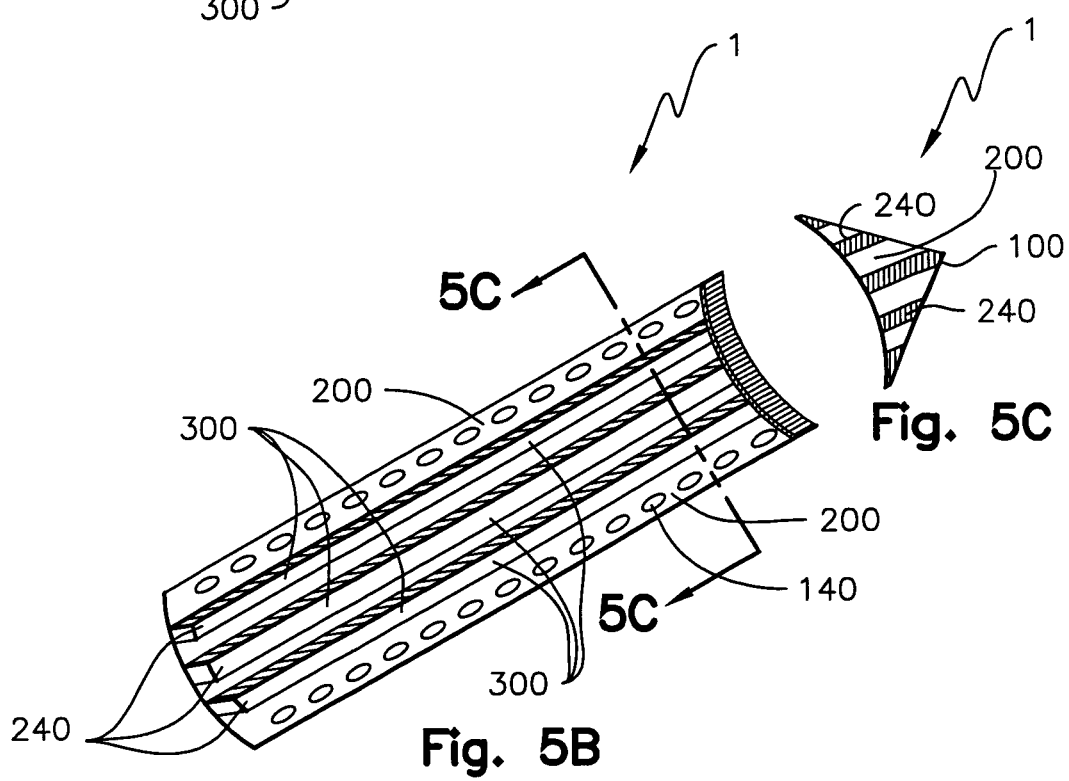
Fig. 5C
Fig. 5B

DRYWALL CORNER OR A TRANSITION CORNER

FIELD OF THE INVENTION

This invention relates generally to drywall construction and particularly to the construction of drywall corners at the bottom or base of the drywall corner and specifically to the transition from a round corner to a right angle corner at a base or bottom of a drywall corner.

BACKGROUND OF THE INVENTION

In wallboard construction, the joint between adjacent sheets of wallboard is usually covered by a paper tape extending lengthwise along the joint. The conventional drywall tape is provided in narrow elongated strips of porous paper wound into rolls. The drywall tape is applied to the joints, and then covered with wet plaster or "mud". The plaster is feathered and smoothed along the edges of the tape to conceal the tape edges and form a smooth unmarred surface where the wallboard adjoins.

It is often necessary to cut the wallboard to form a corner, which thereby exposes the plaster contained between the heavy paper sheets. This exposed plaster tends to crumble unless these edges are protected. To finish exterior corners in wallboard construction, metal corner beads are typically installed. Such corner beads are conventionally formed by rollforming from an elongated strip of sheet metal, and provide a rounded nose with two mounting flanges extending at substantially right angles from the opposing sides of the nose. These mounting flanges often provide a rough surface so that the joint compound will adhere when the corner is finished.

The corner bead is installed by securing the mounting flanges along the surface of the drywall panels adjacent to the corner by nails or the like. Additionally, such flanges may be covered with a tape which is affixed to the wallboard by mud or wet plaster which is smoothed into place to cover the flanges, or flanges and tape.

The finished exterior corners, in wallboard construction, covered with a radiused or arcuate metal corner bead is transitioned, near the floor, from the rounded corner to a 90 degree corner. The drywall 90 degree corner is formed to accommodate carpenters in applying trim at the bottom of drywall and against the floor. The 90 degree corner, at the bottom of the corner, allows the carpenter to perform normal mitering of wood or composites which are used in base molding products. Transition corners typically provide a curved portion mating with the radiused or arcuate metal corner above the floor area and are secured in place by nails or staples through flanges extending on each leg of the approximate 90 degree angle corner. The transition corner is first placed by the workman near the floor and over or under the radiused or arcuate corner with a vertical placement intended by the workman. Invariably the securing of the transition corner, via nails or other such mechanical means, causes a lateral force moving the transition corner away from the vertical. The workman must repeatedly remove securing nails or staples and reposition the transition corner until a vertical placement has been achieved. Such labor intensive effort increases the expense of installing wallboard.

U.S. Pat. No. 6,295,776 to Kunz et al discloses and claims a manufacturing process for a tape-on type corner bead, having an elongated metal core strip with a longitudinal arcuate nose and a pair of flanges extending outwardly from the nose where each flange is covered by a strip of paper bonded to the exterior surface which also comprise wings which project outwardly beyond the extent of the flanges. The paper cover strip is dimensionally stable on contact with wet joint compound. There is no transition from round to right angle demonstrated. U.S. Pat. Pub. No. 2003/0131546 to Kunz discloses and claims the apparatus disclosed in U.S. Pat. No. 6,295,776. U.S. Pat. No. 6,539,680 to Kunz discloses and claims the bead of the apparatus disclosed in U.S. Pat. No. 6,295,776. U.S. Pat. No. 5,138,810 to Kartler discloses a corneraide. U.S. Pat. No. 4,313,991 to Lamb discloses a seam taping member having a bead. U.S. Pat. No. 4,719,732 to Bernard discloses a covering over the 90 degree corner of wallboard which rounds the corner to a small radius. There is no transition from round to right angle disclosed.

The patents referred to herein are provided herewith in an Information Disclosure Statement in accordance with 37 CFR 1.97.

SUMMARY OF THE INVENTION

The finishing process of installing the transition corners of the prior art, at the trim, requires skill and is time consuming with the principal work required in establishing a vertical relationship at the junction between the 90 degree transition and the rounded corner. Any deviation from a 90 degree corner at the bottom of drywall will obstruct efforts of carpenters in their installation of baseboard trim. The transition corner of this invention transitions from a round wallboard exterior corner to a right angle corner at the trim or base or floor. The transition corner comprises an exterior side forming an acute angle less than 90 degrees or a right angle and an arcuate or radiused interior side. The transition corner transitions at the top from the acute angle or right angle to a rounded shape to match the round wallboard exterior corner shape having an arcuate or radiused shape at the interior side to meet and match the rounded exterior corner with an arcuate or radiused interior side matching the radius of the wallboard corner bead. The transition corner at the interior side is coated with adhesive means which allows the workman to place and adjust the transition corner to insure a vertical placement. The transition corner is secured in place by the adhesive means and forms, via depressions or apertures at the exterior side, a receptacle to receive mud.

BRIEF DESCRIPTION OF THE DRAWINGS

The foregoing and other features and advantages of the present invention will become more readily appreciated as the same become better understood by reference to the following detailed description of the preferred embodiment of the invention when taken in conjunction with the accompanying drawings, wherein:

FIG. 1 is a top plan view of the transition corner (1) showing the exterior side (100), the top (120), the bottom (160), depressions (140) and bead (180).

FIG. 1A is a section 1A from FIG. 1 showing the exterior side (100), the depressions (140), the interior side (200), the bead (180) and the angle (220) formed at by the exterior side (100) at the apex (184); the exterior side (100) extends from the longitudinal bead (180) to a conjunction with the interior side (200) and terminates at that conjunction.

FIG. 2 is a side elevation of the transition corner (1) showing the exterior side (100), the top (120), the bottom (160), depressions (140) and bead (180).

FIG. 2A is a top view corner (1) showing the exterior side (100), the top (120), depressions (140) and bead (180).

FIG. 3 is a perspective of the transition corner (1) showing the exterior side (100), the top (120), the bottom (160), depressions (140), bead (180) and transition bead (182).

FIG. 3A is a detail from FIG. 3 showing the exterior side (100), the top (120), depressions (140), bead (180) and transition bead (182).

FIG. 3B is a detail from FIG. 3 showing the exterior side (100), the bottom (160), depressions (140) and bead (180).

FIG. 5A is a view showing the top (120) and bottom (160). An alternative embodiment of the interior side (200) is depicted with horizontal corner ribs (220) having adhesive means (300).

FIG. 5B is a view showing the top (120) and bottom (160). An alternative embodiment of the interior side (200) is depicted with vertical corner ribs (220) having adhesive means (300).

FIG. 5C is a view showing vertical ribs (240) projecting from the exterior side (100) into the interior side (200).

DETAILED DESCRIPTION

Figure 4:
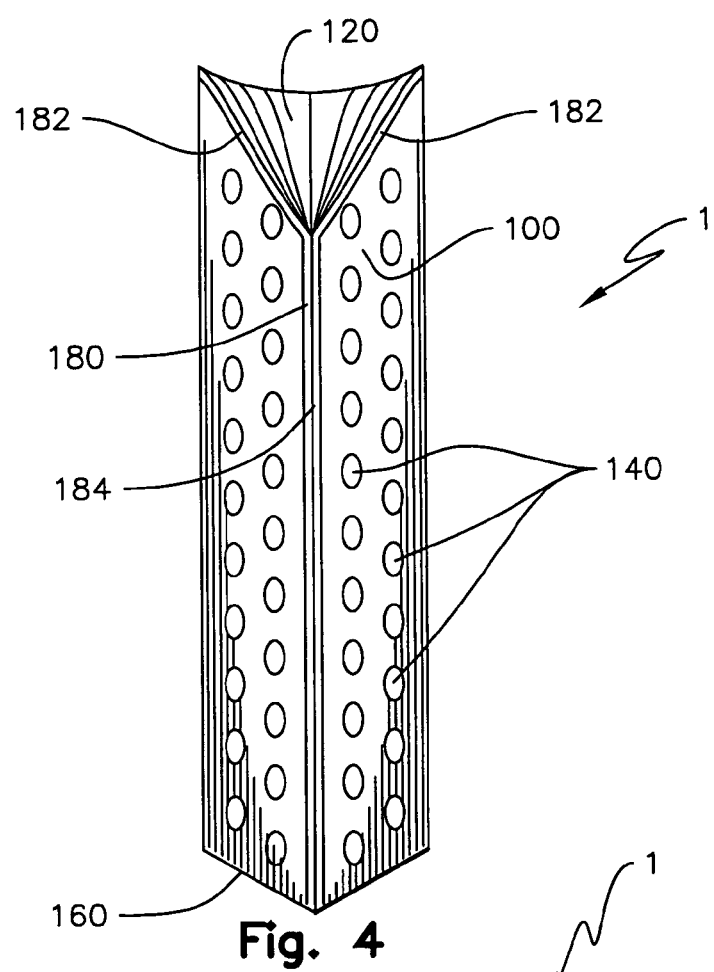
FIG. 4 is a front elevation showing the exterior side (100), the top (120), the bottom (160), depressions (140), bead (180), and transition bead (182).
Figure 5:
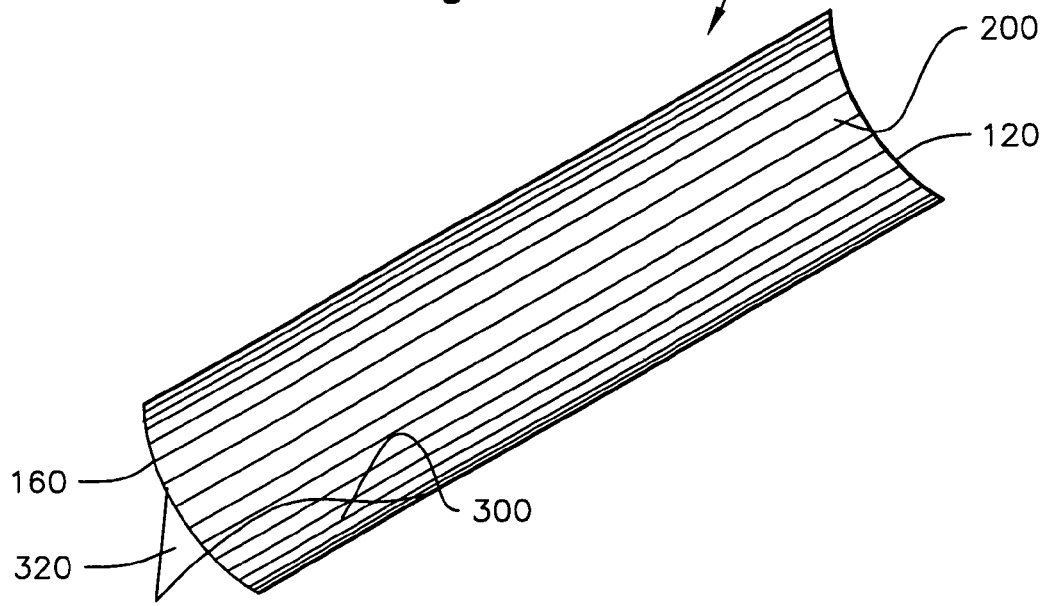
FIG. 5 is a view showing the top (120), bottom (160), interior side (200) and adhesive means (300).

The Drywall Corner (1) is illustrated in FIGS. 1 through 7. FIGS. 1, 1A, 2, 2A, 3, 3A, 3B, 4, 6 and 7 illustrate the Drywall Corner (1) from an exterior side (100) depicting a top (120), a bottom (160), a longitudinal bead (180), a transition bead (182) and depressions (140). The Drywall Corner (1) is elongated and constructed from a rigid or semi-rigid material, including but not limited to metal, wood and plastics with construction, in the preferred embodiment, from injection or other plastic molding processes.

Figure 6:
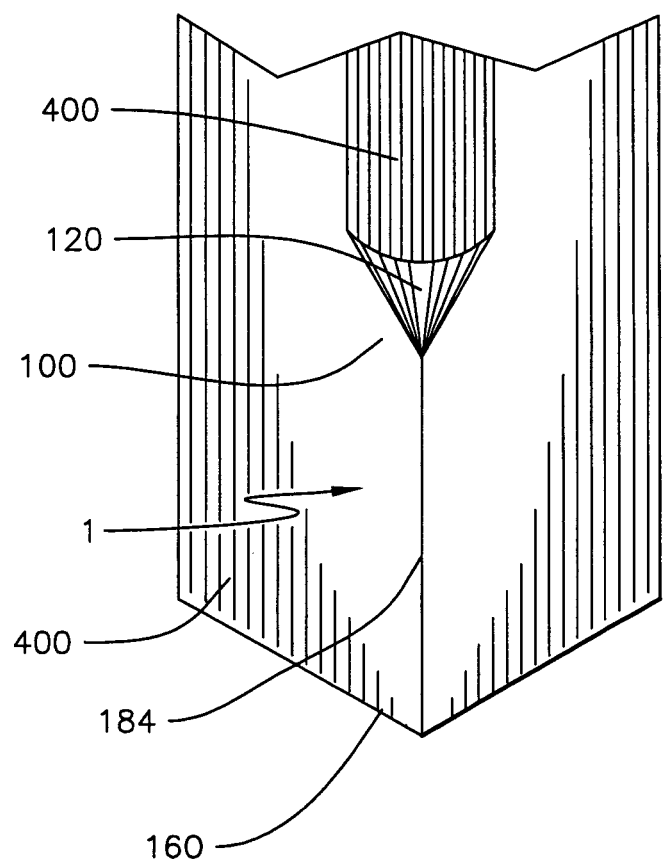
FIG. 6 is a front elevation showing the exterior side (100), the top (120), the bottom (160), depressions (140), bead (180), and transition bead (182) of the drywall corner (1) in position at an exterior wall corner (400).
Figure 7:
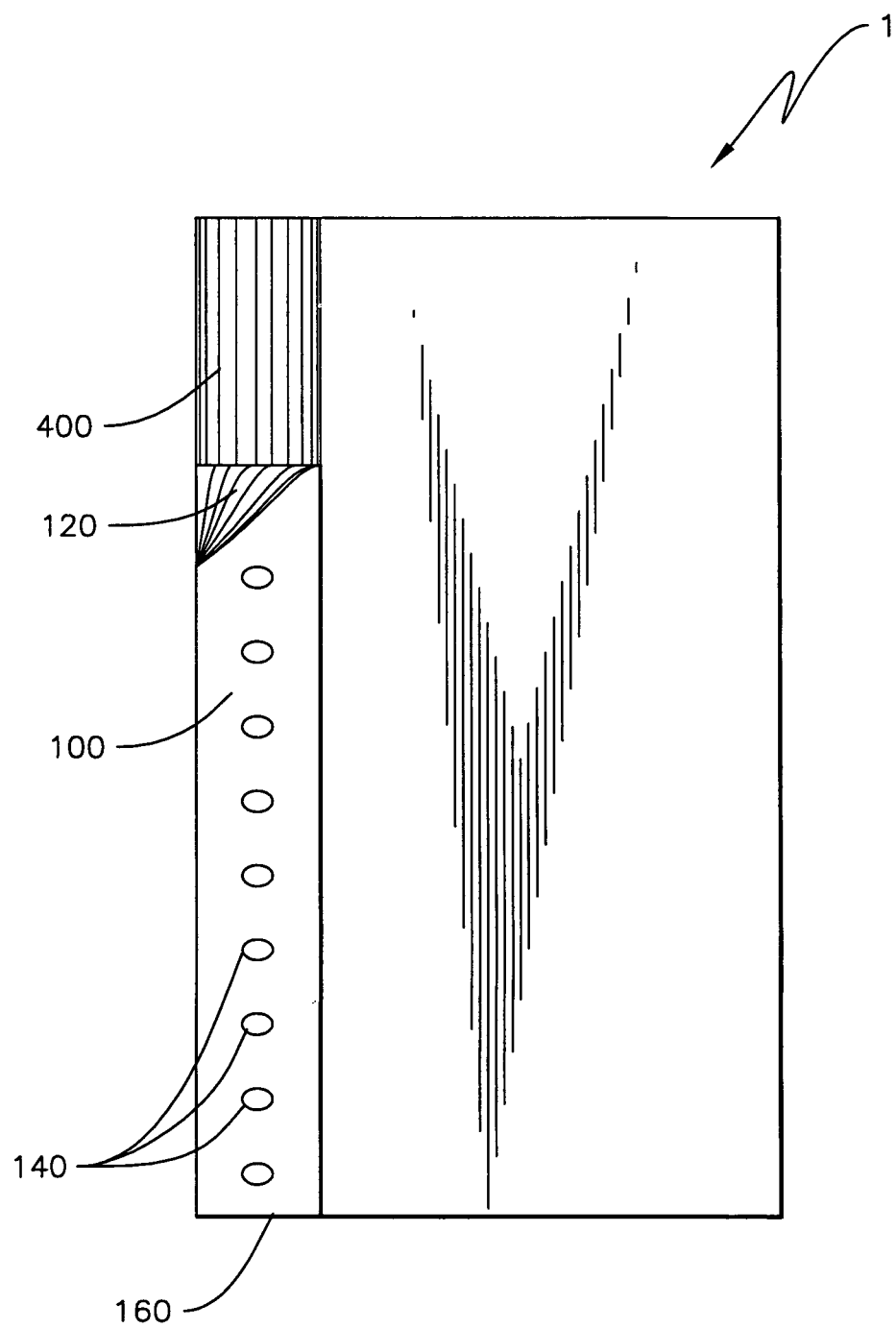
FIG. 7 is a side elevation showing the exterior side (100), the top (120), the bottom (160), depressions (140), bead (180), and transition bead (182) of the drywall corner (1) in position at an exterior wall corner (400).

The elongated Drywall Corner (1) or transition corner (1) forms a frame to allow the transition of a round wallboard exterior corner (400), as seen in FIGS. 6 and 7, to a right angle corner (410) at the trim or base or floor. The transition corner (1) comprises an exterior side (100) forming an acute angle θ (220) generally less than a right angle, a top (120), a bottom (160), depressions at the exterior side (100) and a bead (180) from bottom (160) proceeding toward and ending proximal the top (120). The bead (180) is formed along the apex (184) of the acute angle. An interior side (200) has a shape which will match and receive the an exterior corner (400) and, in the preferred embodiment, the shape is arcuate having a radius matching the radius of the exterior corner (400). The interior side (200) is coated with adhesive means (300) which allows the workman to place and adjust the transition corner (1), to insure a vertical placement, against and in contact with the exterior corner (400). The adhesive means (300) will form, in the preferred embodiment, a permanent adherence to the exterior corner (400) following a lapse of time or upon setup of the adhesive means (300). The adhesive means (300) in the preferred embodiment, will coat the entirety of the interior side (200) and may be temporarily sealed with an adhesive sealing means (320), such as but not limited to a plastic strip (320) which, upon being removed, will expose the interior side (200) and adhesive means (300) for contact with an exterior corner (400). Depression means (140) are formed at the exterior side (100) with said depression means (140) fulfilling a function of receiving mud as mud is applied to the transition corner (1) and to the wall board adjacent to the transition corner. Depression means (140) may be slot like or apertures penetrating the transition corner (1) from the exterior side (100) proximal to but not perforating the interior side (200).

Where the exterior side (100) forms an acute angle θ (220), the combination of depression means (140) and the less than a right angle formation of the exterior side (100) at the apex (184) functions to receive mud thereby increasing the structural integrity between the transition corner (1) and the exterior corner (400).

Alternate embodiments of the transition corner (1) at the interior side (200) include the formation of at least one arcuate horizontal rib (220) coated with adhesive means (300), and with at least three arcuate horizontal ribs (220) as shown in FIG. 5A. The adhesive means (300) may be covered by an adhesive sealing means (320). Another embodiment of the transition corner (1) at the interior side (200) include the formation of at least one vertical rib (240) coated with adhesive means (300) as shown in FIG. 5B where the adhesive means (300) may be covered by an adhesive sealing means (320). Said at least one vertical rib (240) will have an arcuate character which will match the radius of the exterior corner (400) to be contacted. FIG. 5B depicts at least three vertical ribs (240).

The bead (180) extends from the bottom (160) toward the top (120) and terminates proximal the top (120). The bead (180) extends outwardly from the exterior side (100) thereby functioning to assist the workman in feathering mud to a right angle at the apex (184). The transition corner (1) proximal the top (120) and commencing at the termination of the bead (180) transitions at the exterior side (100) from an acute angle θ (220) at the apex (184) to a rounded exterior side (100) which will approximate in appearance the curved shape of the exterior corner (400). A transition bead (182) extends at the top (120) to the right and to the left from the termination of the bead (180). The transition bead (182) extends outwardly from the exterior side (100) at the top (120) thereby functioning to assist the workman in feathering mud to transition from the right angle at the apex (184) and bead (180) to the rounded top (120). The top (120), most distal from the bottom (160), is rounded at the exterior side (100) and top (120) and is arcuate at the interior side (200) to match and receive the exterior corner (400).

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. A transition corner for transitioning between an arcuate exterior corner of a wall to an interior right angle corner of a trim portion, the transition corner comprising:
   a. an interior side opposite an exterior side;
   b. the exterior side having a top face, a bottom, a first face, a second face, a first longitudinal edge, and a second longitudinal edge, the first face and the second face converging at a longitudinal apex of the exterior side, the first face and the second face forming an angle at the longitudinal apex suitable to mate with the trim portion;

i. the first face peripherally bordered by the top face, the bottom, the first longitudinal edge, and the longitudinal apex;
  ii. the second face peripherally bordered by the top face, the bottom, the second longitudinal edge, and the longitudinal apex;
  iii. the first longitudinal edge formed by a conjunction between the interior side and the first face; and
  iv. the second longitudinal edge formed by a conjunction between the interior side and the second face;
  c. the interior side having a continuously curving arc from the first longitudinal edge to the second longitudinal edge, the continuously curving arc having a consistent radius matched to receive a portion of the arcuate exterior corner of the wall; and
  d. the top face of the exterior side peripherally bordered by the interior side, the first face, and the second face, and further:
    i. an arcuate conjunction is formed between the top face and the interior side;
    ii. the top face substantially coming to a point at the conjunction between the top face and the longitudinal apex; and
    iii. the top face transitions between the arcuate conjunction and the conjunction between the top face and the longitudinal apex;
  e. wherein an entirety of the transition corner extends between the first longitudinal edge and the second longitudinal edge; and
  f. further comprising a longitudinal bead extending outwardly from the longitudinal apex.

2. The transition corner of claim 1, the interior side being directly adherable to the portion of the arcuate exterior corner of the wall.

3. The transition corner of claim 1, the interior side suitable for receiving adhesive for adhering the interior side to the arcuate exterior corner of the wall.

4. The transition corner of claim 1 further comprising a first transitional bead extending outwardly from the conjunction between the first face and the top face and a second transitional bead extending outwardly from the conjunction between the second face and the top face.

5. The transition corner of claim 1, wherein the angle at the longitudinal apex is an acute angle.

6. The transition corner of claim 1, wherein the first face and the second face include depressions for receiving mud.

7. The transition corner of claim 1, wherein the first face and the second face include depressions for receiving mud, the depressions having a greater depth at a location proximal to the longitudinal apex and a lesser depth at a location proximal to the first longitudinal edge and the second longitudinal edge.

8. The transition corner of claim 1, wherein the first face and the second face include apertures, the apertures open at the exterior surface of the transition corner and closed at the interior surface of the transition corner.

9. The transition corner of claim 1, wherein the surface of the interior side is substantially smooth.

10. The transition corner of claim 1, the top face being a rounded top face.

11. A transition corner for transitioning between an arcuate exterior corner of a wall to an interior right angle corner of a trim portion, the transition corner comprising:
  a. an interior side opposite an exterior side;
  b. the exterior side having a rounded top face, a bottom, a first face, a second face, a first longitudinal edge, and a second longitudinal edge, the first face and the second face converging at a longitudinal apex of the exterior side, the first face and the second face forming an acute angle at the longitudinal apex:
    i. the first face peripherally bordered by the rounded top face, the bottom, the first longitudinal edge, and the longitudinal apex;
    ii. the second face peripherally bordered by the rounded top face, the bottom, the second longitudinal edge, and the longitudinal apex;
    iii. the first longitudinal edge formed by a conjunction between the interior side and the first face; and
    iv. the second longitudinal edge formed by a conjunction between the interior side and the second face;
  c. the interior side having a continuously curving arc from the first longitudinal edge to the second longitudinal edge, the continuously curving arc having a consistent radius matched to receive a portion of the arcuate exterior corner of the wall;
  d. the rounded top face of the exterior side peripherally bordered by the interior side, the first face, and the second face, and further:
    i. an arcuate conjunction is formed between the rounded top face and the interior side;
    ii. the rounded top face generally coming to a point at the conjunction between the rounded top face and the longitudinal apex; and
    iii. the rounded top face transitions between the arcuate conjunction and the conjunction between the rounded top face and the longitudinal apex;
  e. a longitudinal bead extending outwardly from the longitudinal apex; and
  f. a first transitional bead extending outwardly from the conjunction between the first face and the rounded top face and a second transitional bead extending outwardly from the conjunction between the second face and the rounded top face;
  g. wherein an entirety of the transition corner extends between the first longitudinal edge and the second longitudinal edge.

12. The transition corner of claim 11, wherein the first face and the second face include depressions for receiving mud.

13. The transition corner of claim 11, the interior side suitable for receiving adhesive for adhering the interior side to the arcuate exterior corner of the wall.

* * * * *